(12) United States Patent
Satoh

(10) Patent No.: US 7,335,160 B2
(45) Date of Patent: Feb. 26, 2008

(54) ULTRASONIC TRANSMITTING AND RECEIVING APPARATUS

(75) Inventor: Tomoo Satoh, Kaisei-machi (JP)

(73) Assignee: FUJIFILM Corporation, Tokyo (JP)

( * ) Notice: Subject to any disclaimer, the term of this patent is extended or adjusted under 35 U.S.C. 154(b) by 500 days.

(21) Appl. No.: 10/976,772

(22) Filed: Nov. 1, 2004

(65) Prior Publication Data
US 2005/0101861 A1     May 12, 2005

(30) Foreign Application Priority Data
Nov. 6, 2003    (JP) .............................. 2003-376388

(51) Int. Cl.
*A61B 8/00* (2006.01)
(52) U.S. Cl. ...................... 600/437; 600/438; 600/443; 600/444; 600/447; 600/459
(58) Field of Classification Search ................ 600/437, 600/438, 443, 444, 447, 459
See application file for complete search history.

(56) References Cited

U.S. PATENT DOCUMENTS

| | | | | |
|---|---|---|---|---|
| 5,129,399 | A * | 7/1992 | Hirama ........................ | 600/447 |
| 5,231,573 | A * | 7/1993 | Takamizawa ................ | 600/437 |
| 6,042,546 | A * | 3/2000 | Bae ............................. | 600/447 |
| 6,159,153 | A * | 12/2000 | Dubberstein et al. ....... | 600/443 |
| 6,179,780 | B1 | 1/2001 | Hossack et al. | |
| 6,221,016 | B1* | 4/2001 | Hayakawa ................... | 600/443 |
| 6,248,070 | B1* | 6/2001 | Kanda et al. ............... | 600/443 |
| 6,340,348 | B1* | 1/2002 | Krishnan et al. ........... | 600/447 |
| 6,419,632 | B1* | 7/2002 | Shiki et al. ................. | 600/443 |
| 6,464,638 | B1* | 10/2002 | Adams et al. .............. | 600/443 |
| 2005/0101861 | A1* | 5/2005 | Satoh ........................ | 600/437 |
| 2006/0264753 | A1* | 11/2006 | Fukukita ..................... | 600/447 |
| 2006/0293596 | A1* | 12/2006 | Jago et al. .................. | 600/437 |
| 2007/0055160 | A1* | 3/2007 | Ng .............................. | 600/447 |

FOREIGN PATENT DOCUMENTS

| | | |
|---|---|---|
| JP | 8-38473 A | 2/1996 |
| JP | 3255815 B2 | 11/2001 |
| JP | 3356996 B2 | 10/2002 |

OTHER PUBLICATIONS

Richard E. Davidsen, et al., "Two-dimensional random arrays for real time volumetric imaging", Ultrasonic Imaging, vol. 16, pp. 143-163, Academic Press, 1994.

* cited by examiner

*Primary Examiner*—Brian L. Casler
*Assistant Examiner*—Baisakhi Roy
(74) *Attorney, Agent, or Firm*—Sughrue Mion, PLLC

(57) ABSTRACT

An ultrasonic transmitting and receiving apparatus for performing the multibeam transmission capable of suppressing the increase in withstand voltage of the ultrasonic transducers and power consumption with increase of the number of transmission beams. This apparatus includes an ultrasonic probe, a drive waveform synthesizing unit for generating information on a synthesized drive waveform obtained by synthesizing the drive waveforms with respect to the respective ultrasonic transducers in order to allow the ultrasonic probe to transmit the ultrasonic beams simultaneously in the different directions, transmitting circuits for generating the drive signals according to the information generated by the drive waveform synthesizing unit and in which plural kinds of maximum output voltages are determined so as to correspond to the maximum amplitudes of the drive signals supplied to the respective ultrasonic transducers, and receiving circuits for processing the detection signals outputted from the ultrasonic transducers received the ultrasonic echoes, respectively.

4 Claims, 16 Drawing Sheets

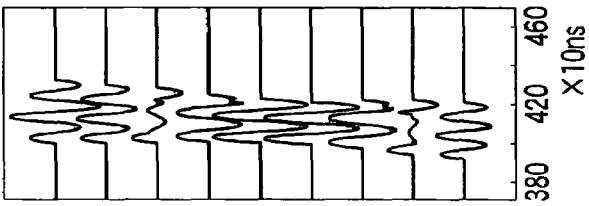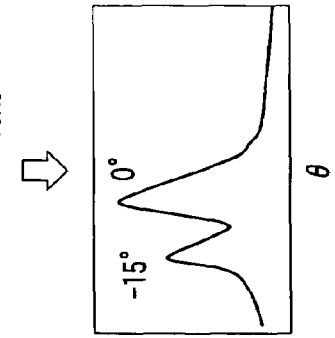
FIG.5A  θ = −15°
FIG.5B  θ = 0°
+
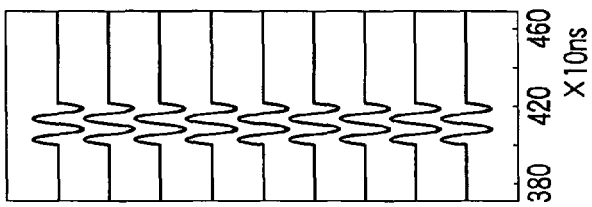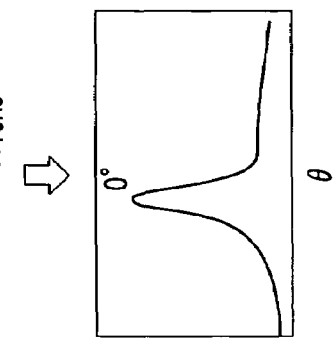
=
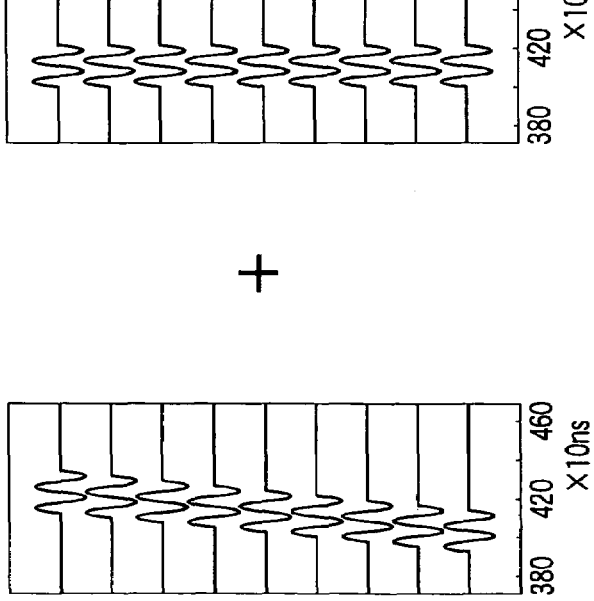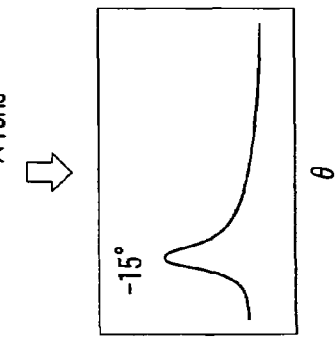
FIG.5C  BIDIRECTIONAL TRANSMISSION

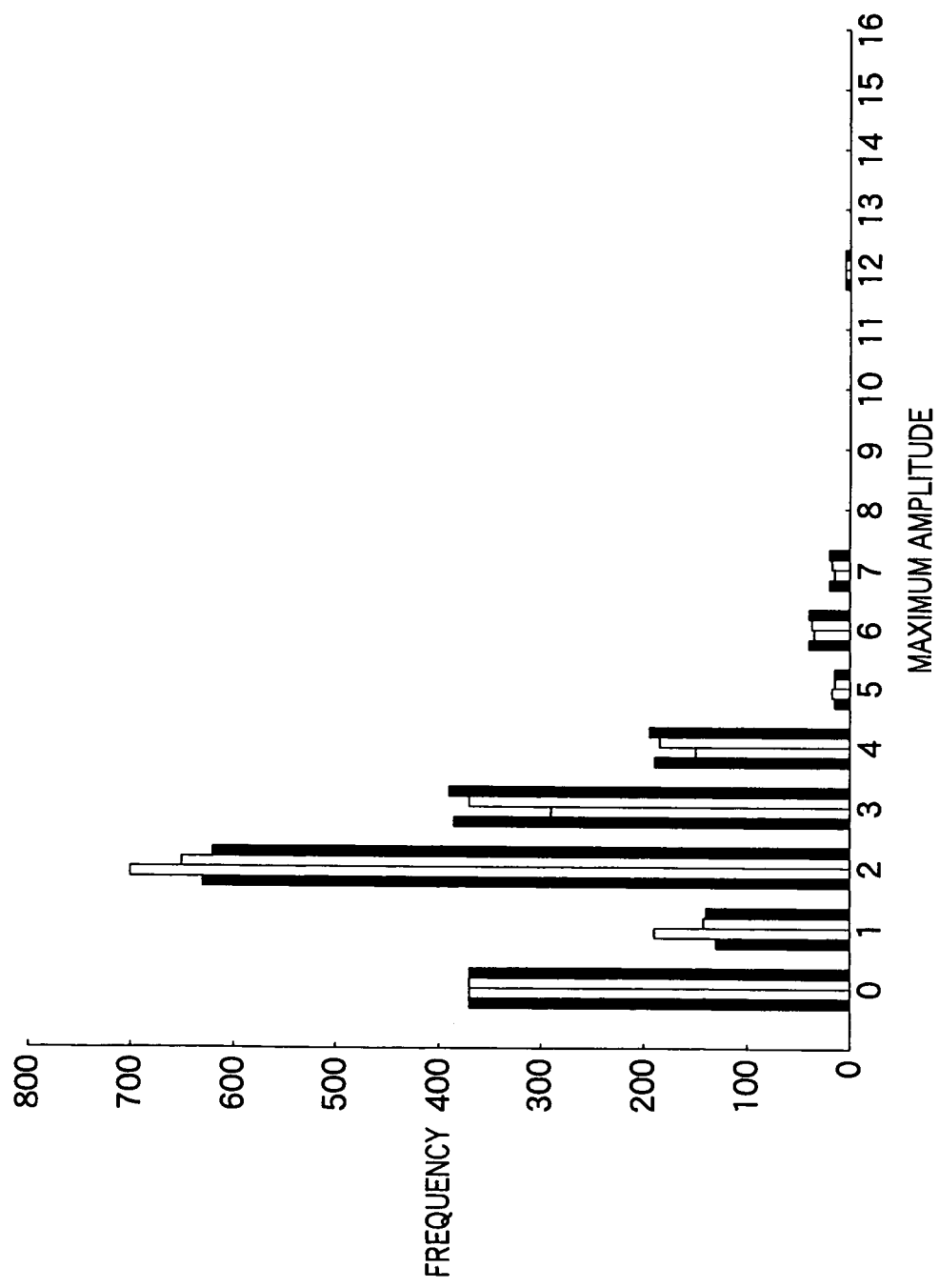

FIG.11

| MAXIMUM AMPLITUDE | 0 | 1 | 2 | 3 | 4 | 5 | 6 | 7 | 8 | 9 | 10 | 11 | 12 | 13 | 14 | 15 | 16 |
|---|---|---|---|---|---|---|---|---|---|---|---|---|---|---|---|---|---|
| DIRECTION (0°, 0°) | 368 | 128 | 627 | 378 | 191 | 16 | 33 | 19 | 0 | 0 | 0 | 0 | 4 | 0 | 0 | 0 | 0 |
| DIRECTION (0°, 14°) | 368 | 189 | 703 | 285 | 151 | 17 | 31 | 16 | 0 | 0 | 0 | 0 | 4 | 0 | 0 | 0 | 0 |
| DIRECTION (14°, 0°) | 368 | 135 | 646 | 359 | 184 | 16 | 35 | 17 | 0 | 0 | 0 | 0 | 4 | 0 | 0 | 0 | 0 |
| DIRECTION (7°, 7°) | 368 | 131 | 620 | 380 | 193 | 16 | 33 | 19 | 0 | 0 | 0 | 0 | 4 | 0 | 0 | 0 | 0 |

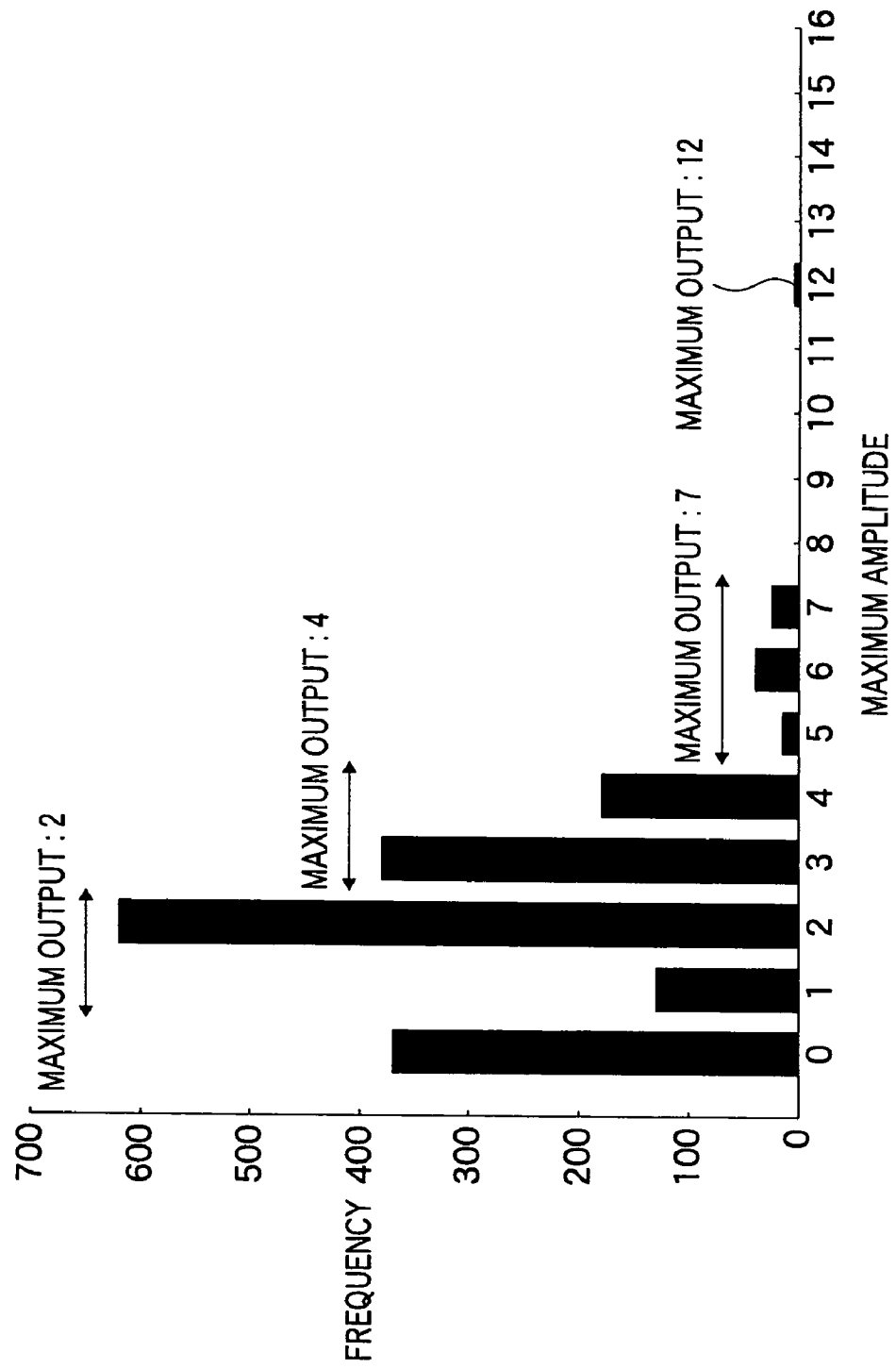

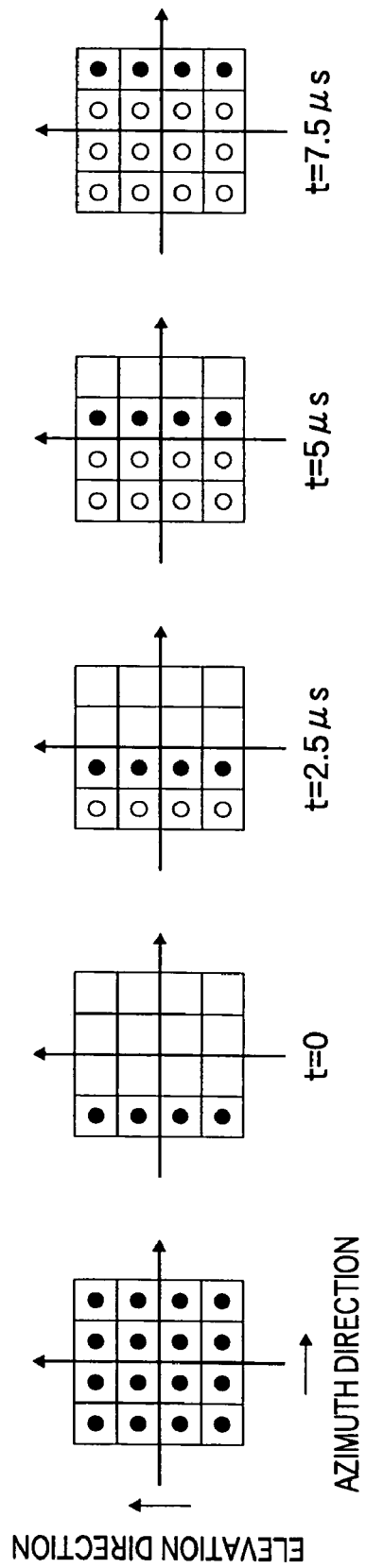

ULTRASONIC TRANSMITTING AND RECEIVING APPARATUS

BACKGROUND OF THE INVENTION

1. Field of the Invention

The present invention relates to an ultrasonic transmitting and receiving apparatus for observing the organs etc. within a living body by transmitting and receiving the ultrasonic waves.

2. Description of a Related Art

Conventionally, in order to acquire a three-dimensional image by transmitting and receiving the ultrasonic waves, using a one-dimensional transducer array with a position sensor, a three-dimensional image is created by electrically steering the transmitted and received ultrasonic waves so as to acquire a two-dimensional images with respect to a section in a depth direction, and further, synthesizing the two-dimensional images acquired by mechanically moving the one-dimensional transducer array. However, according to the technique, since there is a time lag in the mechanical movement of the one-dimensional transducer array, the two-dimensional images at different times are synthesized, so that the synthesized image becomes blurred. Therefore, the technique is unsuitable for imaging of an object with a movement such as a living body.

In order to solve such a defect, it is more advantageous to acquire a three-dimensional image using a two-dimensional transducer array. Richard E. Davidsen et al., "TWO-DIMENSIONAL RANDOM ARRAYS FOR REAL TIME VOLUMETRIC IMAGING", ULTRASONIC IMAGING, Vol. 16 (U.S.), Academic Press, 1994, pp. 143-163 discloses the multibeam reception using a two-dimensional transducer array for transmitting the ultrasonic beams to one region and simultaneously receiving the ultrasonic echoes reflected from 16 directions within the region and processing them. Further, U.S. Pat. No. 6,179,780 discloses the multibeam transmission for simultaneously transmitting the ultrasonic beams to a plurality of regions.

Furthermore, JP-A-8-38473 discloses an ultrasonic diagnosing apparatus capable of simultaneously generating the ultrasonic transmission beams having different frequency bands, focal ranges and orientations by generating the transmission signals having different frequency bands for one transmission. However, since the maximum amplitude of the transmission signal increases by synthesizing the frequency signals, it is necessary to increase the withstand voltage of the ultrasonic transducer, and it is also necessary to increase the maximum output voltage of the transmission signal generating circuit, and thereby, the power consumption also increases.

On the other hand, JP-B-3356996 discloses an ultrasonic diagnosing apparatus for simultaneously forming the transmission beams without the need of any special driver or the like. In the ultrasonic diagnosing apparatus, in order to form the transmission beams by one transmission, a plurality of vibrating elements are divided into a plurality of transmission groups, and the transmitting circuits for supplying a plurality of transmission signals having different transmission frequencies with respect to the respective transmission group are included.

Similarly, JP-B-3255815 discloses an underwater sonar equipment having an ultrasonic wave transmitter/receiver in which the circular vibrating surfaces can be separately arranged, but not occupying a large area. In this underwater sonar equipment, the transmitter/receiver is formed by arranging the ultrasonic vibrators so that all of their vibrating surfaces may be located within the first circle along the horizontal surface. A desired beam can be formed while keeping the occupied area of the vibrating surfaces of the ultrasonic vibrators small by grouping these ultrasonic vibrators into the first to sixth ultrasonic vibrator groups with the second to fifth circles inscribed in the first circle and having the same diameter smaller than the first circle, and driving these ultrasonic vibrator groups appropriately and selectively.

However, as disclosed in JP-B-3356996 and JP-B-3255815, when the multibeam transmission is performed in a state in which the vibrators are divided into the groups, there is a problem that the intensity of each transmission beam becomes lower.

SUMMARY OF THE INVENTION

Accordingly, in view of the above described points, the present invention is objected to suppress the increase in withstand voltage of the ultrasonic transducers and power consumption with increase of the number of transmission beams in the ultrasonic transmitting and receiving apparatus for performing the multibeam transmission.

In order to solve the above-described problems, an ultrasonic transmitting and receiving apparatus according to the present invention includes: an ultrasonic probe including a plurality of ultrasonic transducers for forming ultrasonic beams according to a plurality of drive signals so as to transmit the ultrasonic beams to an object to be inspected, and receiving ultrasonic echoes reflected from the object so as to output a plurality of detection signals, respectively; drive waveform synthesizing means for generating information on a synthesized drive waveform obtained by synthesizing a plurality of drive waveforms with respect to each of the ultrasonic transducers in order to allow the ultrasonic probe to transmit a plurality of ultrasonic beams simultaneously in a plurality of different directions; a plurality of transmitting circuits for generating a plurality of drive signals according to the information generated by the drive waveform synthesizing means so as to supply the plurality of drive signals to the plurality of ultrasonic transducers, respectively, plural kinds of maximum output voltages being determined so as to correspond to maximum amplitudes of the drive signals supplied to the respective ultrasonic transducers; and a plurality of receiving circuits for processing the plurality of detection signals outputted from the plurality of ultrasonic transducers which have received the ultrasonic echoes, respectively.

According to the ultrasonic transmitting and receiving apparatus for performing the multibeam transmission according to the present invention, by determining the plural kinds of maximum output voltages with respect to the transmitting circuits so as to correspond to the maximum amplitudes of the drive signals supplied to the respective ultrasonic transducers, the increase in withstand voltage of the ultrasonic transducers and power consumption with increase of the number of transmission beams can be suppressed. Note that, in this application, the transducer for one element that forms the transducer array is referred to as "ultrasonic transducer".

BRIEF DESCRIPTION OF THE DRAWINGS

FIG. 5A-5C shows the relationships between the drive waveforms applied to the ultrasonic transducers and the ultrasonic beams generated by the drive waveforms;

FIG. 10 is a histogram showing the maximum amplitudes of the drive signals applied to the respective ultrasonic transducers for transmitting 16 ultrasonic beams;

FIG. 11 is a table showing the maximum amplitudes of the drive signals applied to the respective ultrasonic transducers for transmitting 16 ultrasonic beams;

FIG. 12 is a diagram for explanation of an example of the power consumption reduction in the multibeam transmission;

FIGS. 16A to 16E are diagrams for explanation of a transmitting method when four transmission beams in the elevation direction are transmitted at intervals of 2.5 µs as one set.

DESCRIPTION OF THE PREFERRED EMBODIMENTS

Figure 1:
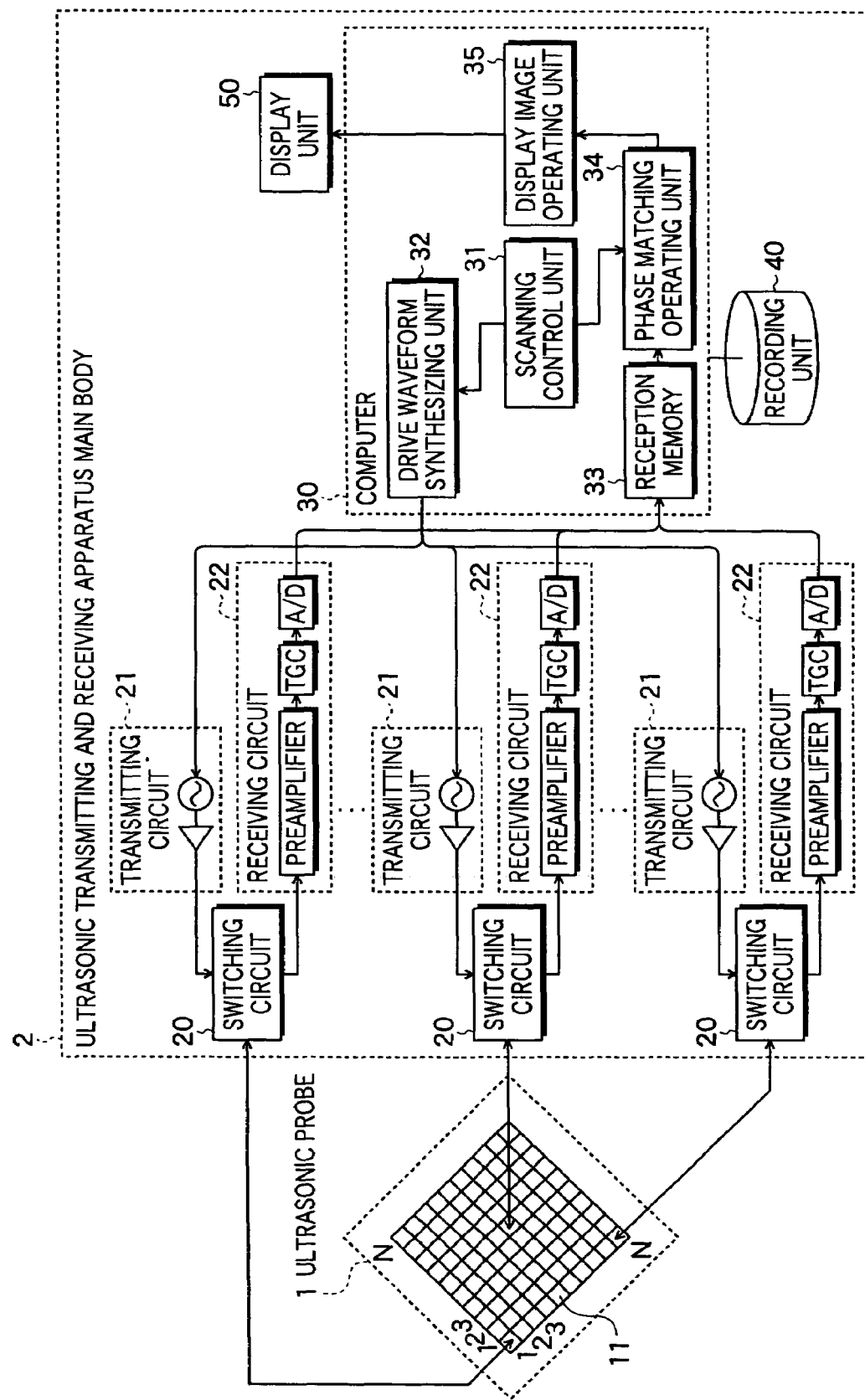
FIG. 1 is a block diagram showing the constitution of an ultrasonic transmitting and receiving apparatus according to one embodiment of the present invention.

Hereinafter, the best mode of the present invention will be described in detail by referring to the drawings. The same component elements are assigned with the same reference numbers and the description thereof will be omitted.

FIG. 1 is a block diagram showing the constitution of an ultrasonic transmitting and receiving apparatus according to one embodiment of the present invention. As shown in FIG. 1, the ultrasonic transmitting and receiving apparatus includes an ultrasonic probe 1 used by being abutted on an object to be inspected, and an ultrasonic transmitting and receiving apparatus main body 2 connected to the ultrasonic probe 1.

The ultrasonic probe 1 has a transducer array (also referred to as "array transducer") including $N^2$ ultrasonic transducers 11 arranged in a two-dimensional matrix form built-in. These ultrasonic transducers 11 are connected to the ultrasonic transmitting and receiving apparatus main body 2 via signal lines.

Each of the ultrasonic transducers 11 is constituted by a vibrator in which electrodes are formed on both ends of a material which has a piezoelectric property (piezoelectric element) such as a piezoelectric ceramic represented by PZT (Pb (lead) zirconatetitanate), a polymeric piezoelectric element represented by PVDF (polyvinylidene difluoride), or the like. Further, a piezoelectric element including a monocrystal of PZNT (an oxide containing lead, zinc, niobium, titanium), which is expected to contribute to the improvements in the sensitivity and bandwidth of the ultrasonic transducer in recent years, may be used.

When a voltage is applied between the electrodes of the vibrator by transmitting the pulse or continuous wave electric signals, the piezoelectric element expands and contracts. By the expansion and contraction, the pulse or continuous wave ultrasonic waves are generated from the respective vibrators, and an ultrasonic beam is formed by synthesizing these ultrasonic waves. Further, the respective vibrators expand and contract by receiving the propagating ultrasonic waves and generate electric signals. These electric signals are outputted as detection signals of the ultrasonic waves.

The ultrasonic transmitting and receiving apparatus main body 2 includes switching circuits 20, transmitting circuits 21, receiving circuits 22, a computer 30, a recording unit 40, and a display unit 50.

The switching circuits 20 connect the ultrasonic transducers 11 built in the ultrasonic probe 1 to the transmitting circuits 21, respectively, at the time of the transmission of the ultrasonic waves, and connect the ultrasonic transducers 11 built in the ultrasonic probe 1 to the receiving circuits 22, respectively, at the time of the reception of the ultrasonic waves.

Each of the transmitting circuits 21 includes a signal generator and an A-class power amplifier. The signal generator generates a drive signal having a delay amount which corresponds to the location of each ultrasonic transducer 11 or the like, according to information on the drive waveform supplied from the computer 30. The power amplifier amplifies the drive signal and supplies it to the ultrasonic prove 1.

Each of the receiving circuits 22 includes a preamplifier, a TGC (time gain compensation) amplifier, and an A/D (analog/digital) converter. The detection signal outputted from each ultrasonic transducer 11 is amplified by the preamplifier, and subjected to the attenuation correction depending on the distance that the ultrasonic waves reach within the object, by the TGC amplifier.

The detection signal outputted from the TGC amplifier is converted into a digital signal by the A/D converter. As a sampling frequency of the A/D converter, at least about a tenfold frequency of the frequency of the ultrasonic wave is required, and a 16-fold or more frequency of the frequency of the ultrasonic wave is desirable. Further, as the resolving power of the A/D converter, the resolving power of ten or more bits is desirable.

The computer 30 controls the transmission and reception of the ultrasonic waves based on software (control program) recorded in the recording unit 40. As the recording unit 40, a recording medium such as a hard disk, a flexible disk, an MO, an MT, a RAM, a CD-ROM, or a DVD-ROM can be used. The computer 30 and the software realize a scanning control unit 31, a drive waveform synthesizing unit 32, a phase matching operating unit 34, and a display image operating unit 35 as a functional block. Further, the computer 30 has a reception memory 33.

The scanning control unit 31 sets the transmission directions of the ultrasonic beams and the reception directions of the ultrasonic echoes sequentially. For example, the scanning control unit 31 controls the drive waveform synthesizing unit 32 to change the directions of a plurality of ultrasonic beams, which are transmitted from the ultrasonic probe 1, with a constant offset according to a predetermined scanning method, or according to a predetermined beam scanning order. The drive waveform synthesizing unit 32 generates information on a synthesized drive waveform formed by synthesizing the drive waveforms with respect to the respective ultrasonic transducers 11 under the control of the scanning control unit 31. The transmitting circuits 21 generate the drive signals based on the information, and thereby, the transmission focusing processing is performed and a plurality of ultrasonic beams are simultaneously transmitted from the ultrasonic probe 1 toward different directions.

The reception memory 33 stores the digital detection signals outputted from the A/D converters of the receiving circuits with respect to the respective ultrasonic transducers in chronological order. The phase matching operating unit 34 performs the reception focusing processing by selecting a predetermined pattern of the reception delay patterns, which have been stored in the recording unit 40, based on the reception direction set in the scanning control unit 31, and providing delays to the plural detection signals based on the pattern and adding the signals. By the reception focusing processing, sound ray data in which the focus of the ultrasonic echoes is narrowed down is formed. By the way, the reception focusing processing may be performed before the A/D conversion or before the correction by the TGC amplifier.

The display image operating unit 35 generates image data based on the sound ray data formed by the phase matching operating unit 34. The display unit 50 includes a display device such as a CRT or an LCD, for example, and displays ultrasonic images based on the image data generated by the display image operating unit 35.

Figure 2:
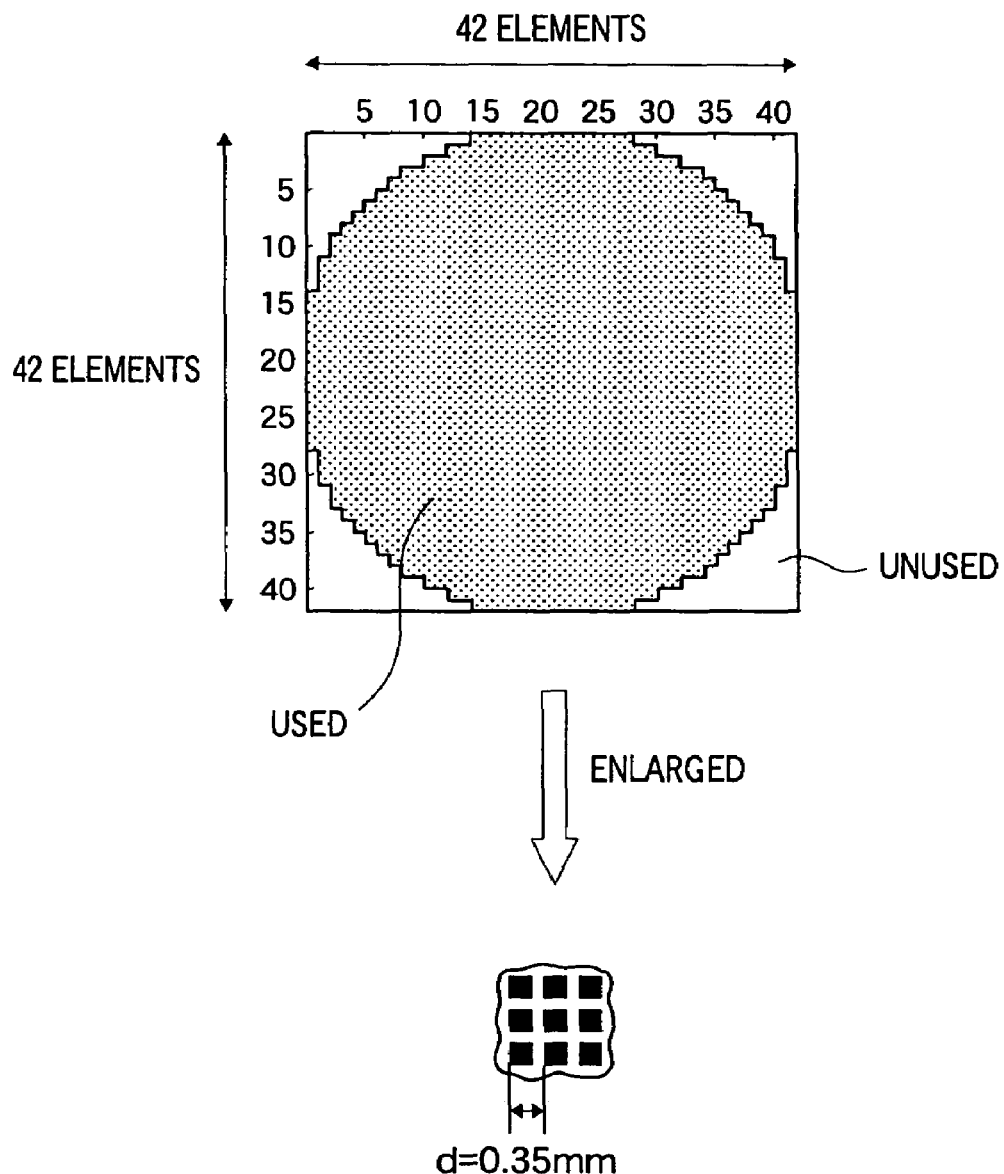
FIG. 2 shows a two-dimensional transducer array for transmission and reception used in the ultrasonic transmitting and receiving apparatus in FIG. 1 as an example.

Next, the reduction of the drive voltages in the multibeam transmission as a feature of the present invention will be described. As a premise of the concept of the present invention, a two-dimensional transducer array for transmission and reception as shown in FIG. 2 will be described as an example. In this example, the number of ultrasonic transducers (elements) is set to 42 elements×42 elements, and the nearly circular part except the four corners of the transducer array is used for the transmission and reception of the ultrasonic waves. Assuming that the element pitch d is 0.35 mm, and the frequency $f_c$ of the ultrasonic wave is 2.5 MHz (wavelength $\lambda$=0.6 mm), the element pitch is equivalent to about 0.58 $\lambda$. Accordingly, the aperture of the ultrasonic probe 1 becomes a circle having a diameter equal to or more than 0.35 mm×42 elements=14.7 mm.

Figure 3:
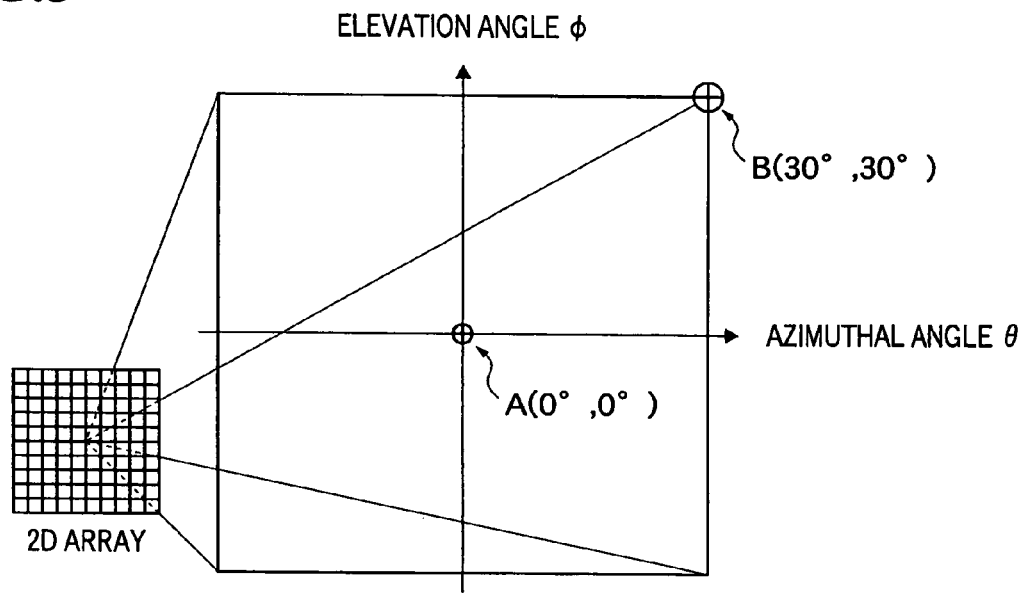
FIG. 3 is a schematic diagram showing a state in which the ultrasonic beams are transmitted from the two-dimensional transducer array to certain points within a scanning range.
Figure 4:
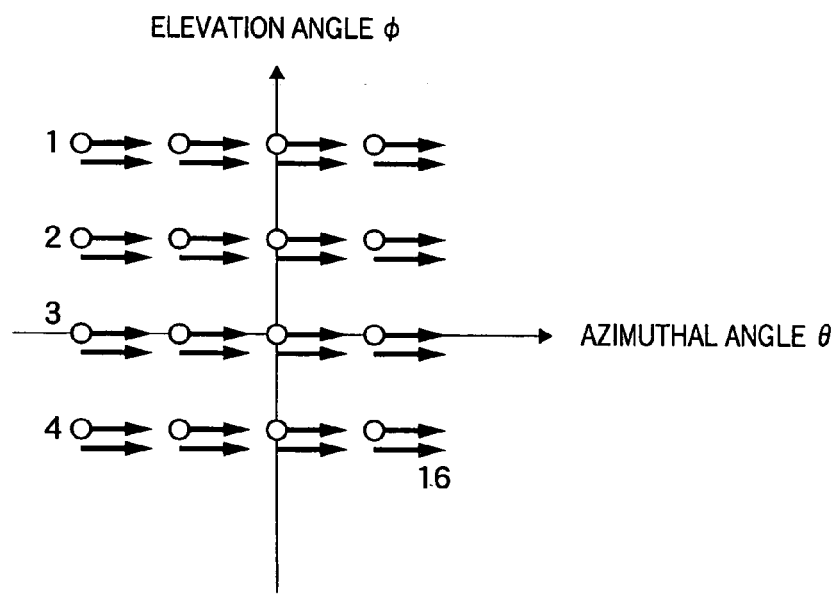
FIG. 4 schematically shows the multibeam transmitted from the two-dimensional transducer array.

FIG. 3 is a schematic diagram showing a state in which the ultrasonic beams are transmitted from the two-dimensional transducer array to certain points within the scanning range. Point A and Point B become focal positions in a spatial region sector-scanned by the ultrasonic beams, respectively. Here, expressing a direction of the focal point in the spatial region using an azimuthal angle $\theta$ and an elevation angle $\phi$, the directions of Point A and Point B are expressed by (0°,0°) and (30°,30°), respectively. In this example, the scanning ranges of the ultrasonic waves are set to $-30°\leq\theta\leq30°$ and $-30°\leq\phi\leq30°$. Further, 16 ultrasonic beams are simultaneously transmitted and the angular differences $\Delta\theta$ and $\Delta\phi$ between these ultrasonic beams are set to 15°, respectively. These ultrasonic beams are sequentially steered at the scanning step $\delta\theta=\delta\phi=1°$. In FIG. 4, 16 ultrasonic beams oriented to the first transmitting direction and 16 ultrasonic beams steered below by certain steps are shown schematically.

FIG. 5 shows the relationships between the drive waveforms applied to the ultrasonic transducers and the ultrasonic beams generated by the drive waveforms. FIG. 5(a) shows that an ultrasonic beam is transmitted toward the azimuthal angle $\theta=-15°$ by applying a plurality of drive signals having different phases to the ultrasonic transducers, respectively. FIG. 5(b) shows that an ultrasonic beam is transmitted toward the azimuthal angle $\theta=0°$ by applying a plurality of equiphase drive signals to the ultrasonic transducers, respectively. FIG. 5(C) shows that an ultrasonic beam oriented toward the azimuthal angle $\theta=-15°$ and an ultrasonic beam oriented toward the azimuthal angle $\theta=0°$ are simultaneously transmitted by synthesizing the drive signals shown in FIG. 5(a) and (b).

As shown in FIG. 5(c), by synthesizing two kinds of drive waveforms, two ultrasonic beams can be simultaneously transmitted. However, at a part where the peaks of the drive waveforms are superposed, the height of the peak is doubled. Generally, in order to simultaneously transmit M ultrasonic beams, there is a possibility that the height of the peak of the drive waveform increases M-fold, so that it is necessary to increase the withstand voltage of the ultrasonic transducers and the maximum output voltage of the transmitting circuits. Especially, in the case of using the A-class power amplifier in the transmitting circuit, power is consumed even when no drive signal is outputted, so that there is a problem that the power consumption becomes higher in proportion to the maximum output voltage. Accordingly, the ultrasonic transmitting and receiving apparatus according to the present invention is characterized in that the peak height of the drive waveform is made as lower as possible even in the case where M ultrasonic beams are simultaneously transmitted.

Next, a simulation that supports the present invention will be described. In this simulation, the delay amount to be provided to the drive signal is obtained based on the distance from each ultrasonic transducer to the focal point and, in order to simultaneously transmit 16 ultrasonic beams toward 16 focal points, the maximum amplitude (the maximum value of the zero-to-peak amplitude) when 16 kinds of drive signals are superposed is calculated. Here, a burst signal having a wave train length of "2" is assumed as the drive signal, and the accuracy of the delay amount provided to the drive signal is set to 10 ns.

Assuming a two-dimensional transducer array having a transmitting surface along the x-y plane, the center of the transmitting surface of the transducer array is given as the original point, and the distance from the original point to a focal point is given as "r". The delay amount τ to be provided to the drive signal in order to transmit an ultrasonic beam from an ultrasonic transducer of the transducer array in the position (x,y,0) toward the focal point in the position $(X_{FOCUS}, Y_{FOCUS}, Z_{FOCUS})$ is expressed by the following equation. Here, the sound speed within the object is "c".

$$\tau = r - \{(X_{FOCUS}-x)^2 + (Y_{FOCUS}-y)^2 + Z_{FOCUS}^2\}^{1/2}/c$$

Further, the position of the focal point is expressed using the azimuthal angle θ and the elevation angle φ as follows.

$$X_{FOCUS} = r \cdot \cos\phi \cdot \sin\theta$$

$$Y_{FOCUS} = r \cdot \sin\phi$$

$$Z_{FOCUS} = r \cdot \cos\phi \cdot \cos\theta$$

Figure 6A:
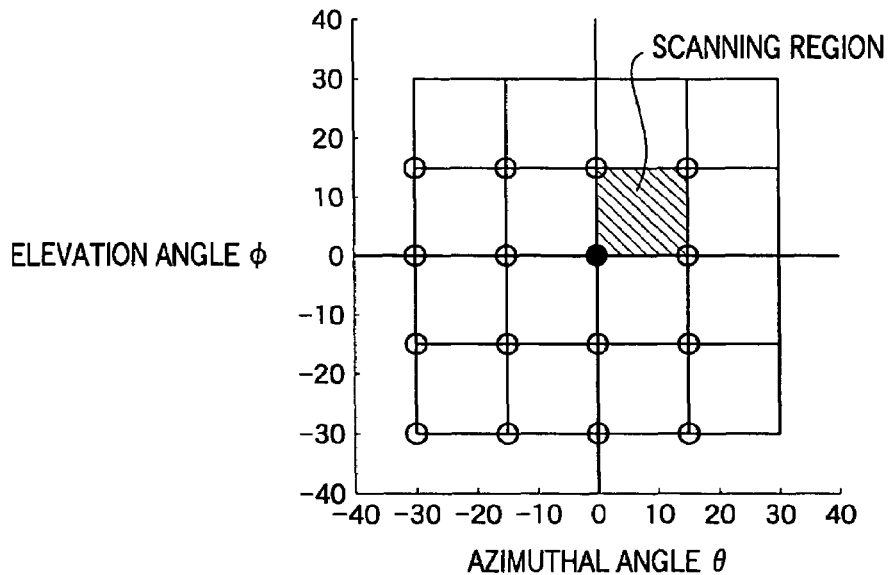
FIG. 6A shows the scanning region and the focal position in the case where a reference ultrasonic beam is transmitted toward direction (0°,0°)
Figure 6B:
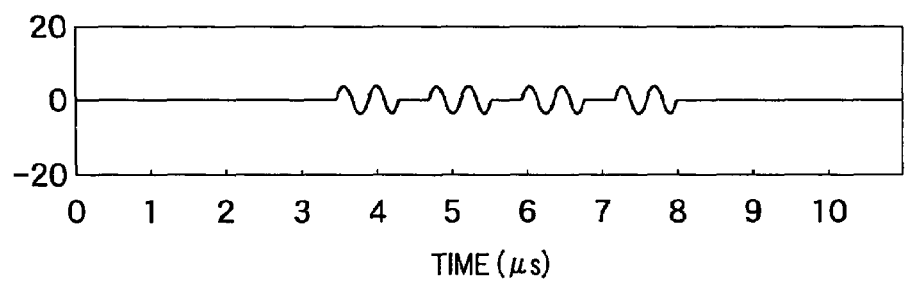
FIGS. 6B to 6D show the waveforms of the drive signals in the case where the reference ultrasonic beam is transmitted toward direction (0°,0°)
Figure 6C:
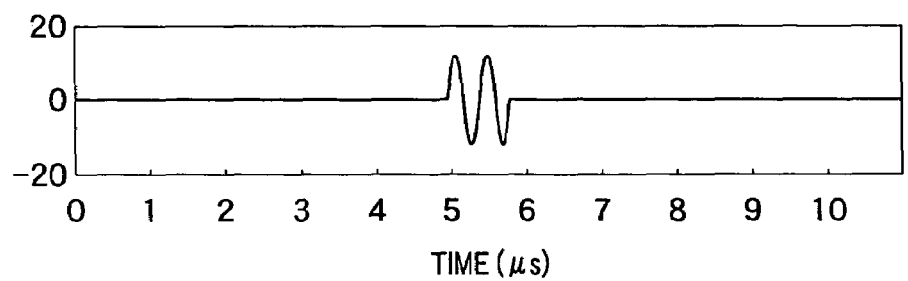
Figure 6D:
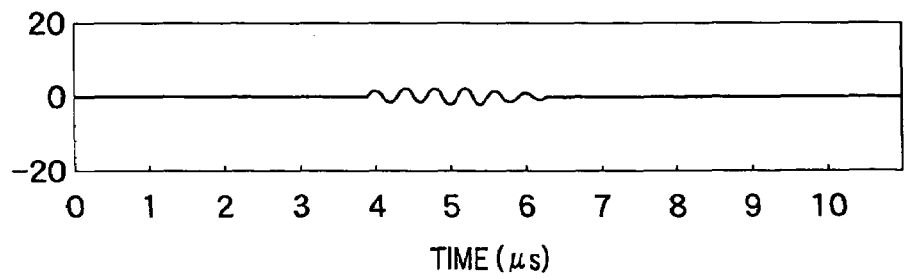
Figure 7A:
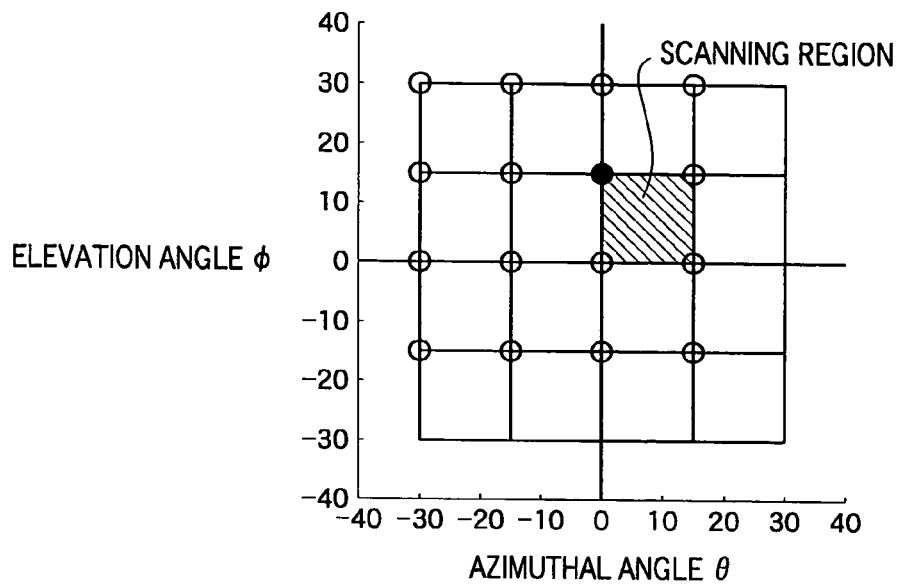
FIG. 7A shows the scanning region and the focal position in the case where the reference ultrasonic beam is transmitted toward direction (0°,14°)
Figure 7B:
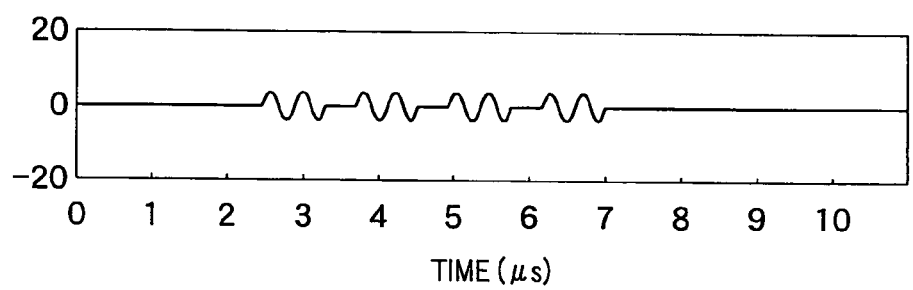
FIGS. 7B to 7D show the waveforms of the drive signals in the case where the reference ultrasonic beam is transmitted toward direction (0°,14°)
Figure 7C:
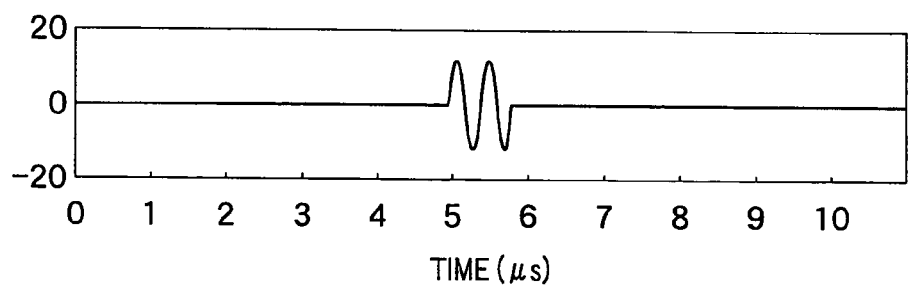
Figure 7D:
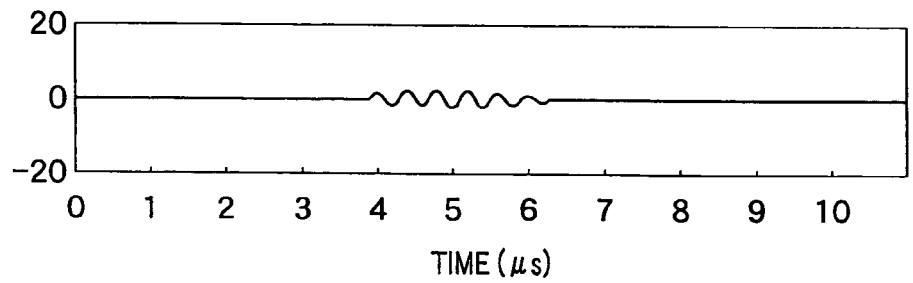

FIG. 6A shows the case where a reference ultrasonic beam of 16 ultrasonic beams is transmitted toward the direction (0°,0°), and the shaded area shows the scanning region scanned by the reference ultrasonic beam. FIGS. 6B to 6D show the waveforms of the drive signals applied to three ultrasonic transducers at the time of the transmission as examples. Further, FIG. 7A shows the case where the reference ultrasonic beam of 16 ultrasonic beams is transmitted toward the direction (0°,14°), and FIGS. 7B to 7D show the waveforms of the drive signals applied to three ultrasonic transducers at the time of the transmission as examples.

Figure 8A:
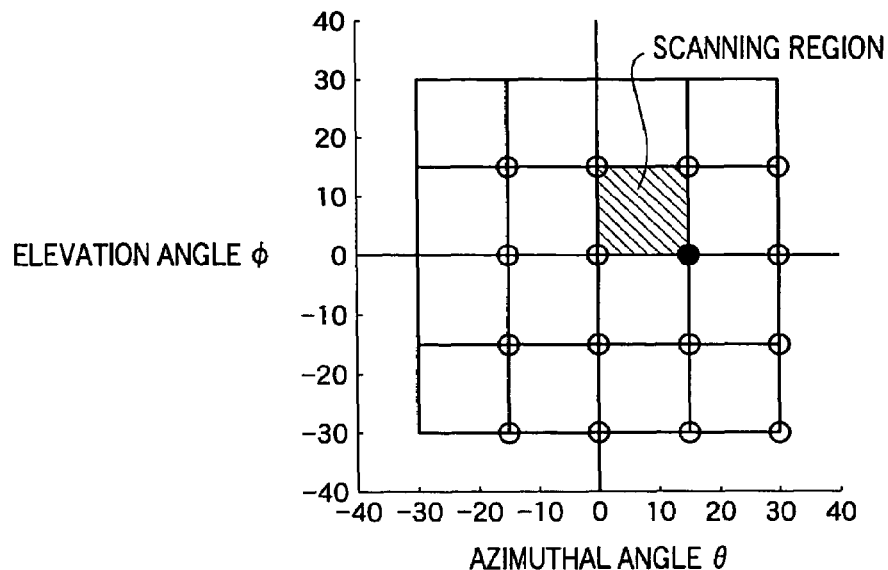
FIG. 8A shows the scanning region and the focal position in the case where the reference ultrasonic beam is transmitted toward direction (14°,0°)
Figure 8B:
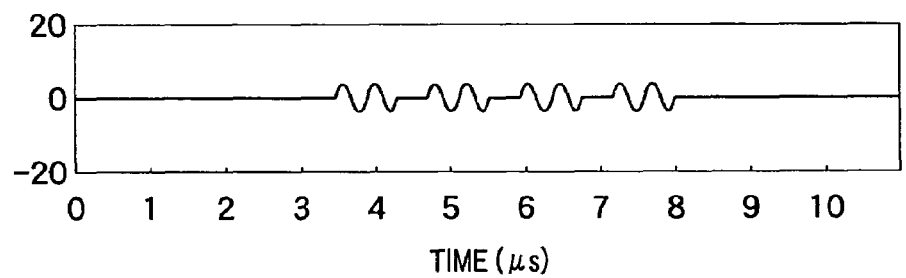
FIGS. 8B to 8D show the waveforms of the drive signals in the case where the reference ultrasonic beam is transmitted toward direction (14°,0°)
Figure 8C:
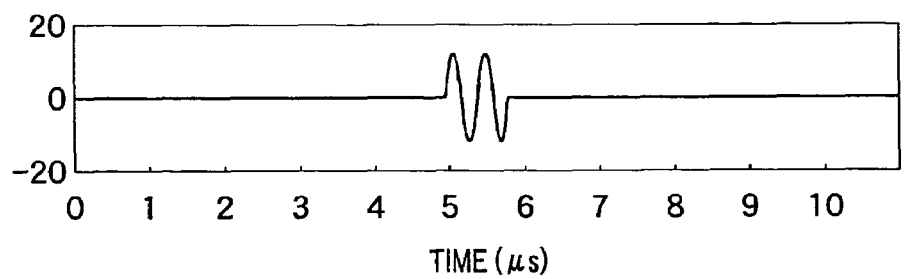
Figure 8D:
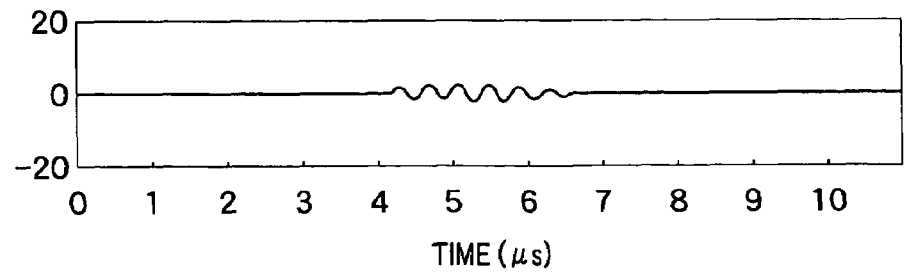
Figure 9A:
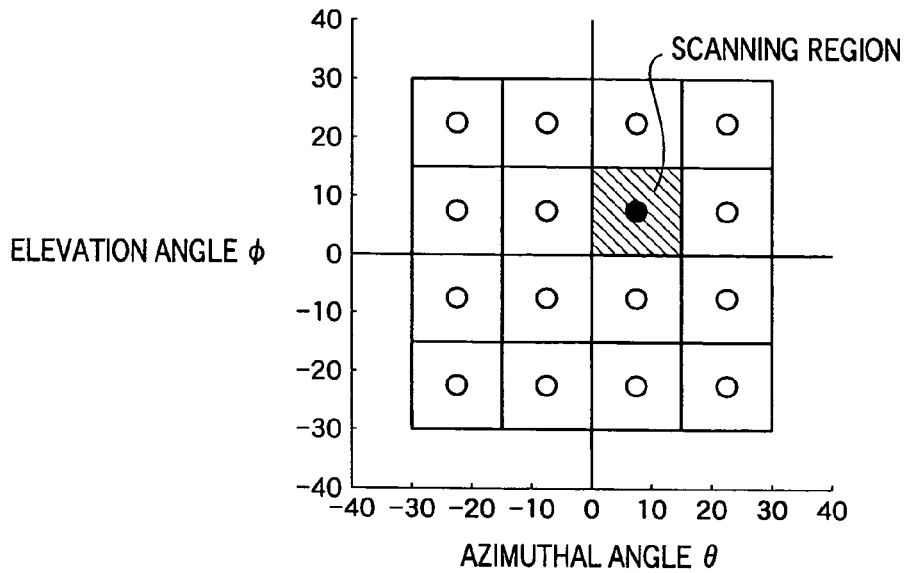
FIG. 9A shows the scanning region and the focal position in the case where the reference ultrasonic beam is transmitted toward direction (7°,7°)
Figure 9B:
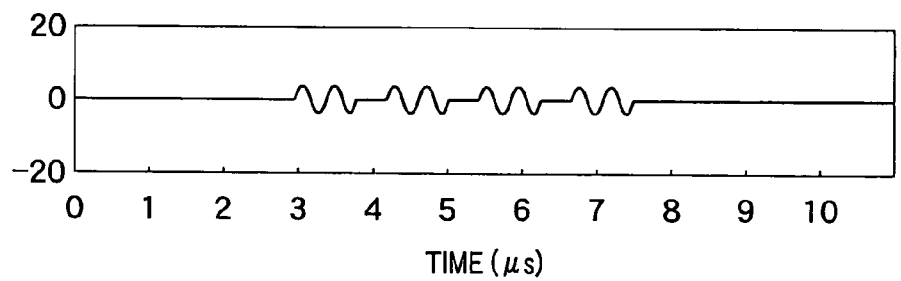
FIGS. 9B to 9D show the waveforms of the drive signals in the case where the reference ultrasonic beam is transmitted toward direction (7°,7°)
Figure 9C:
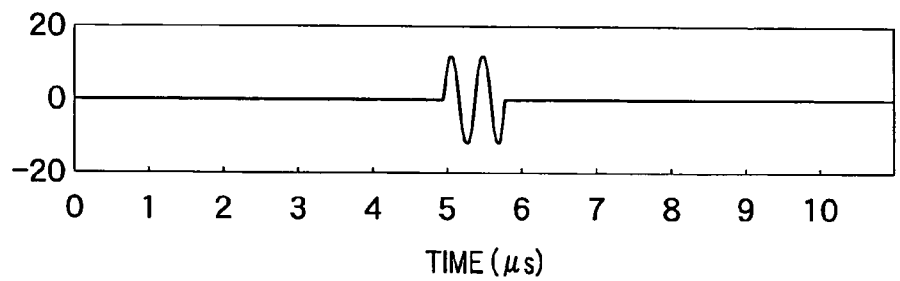
Figure 9D:
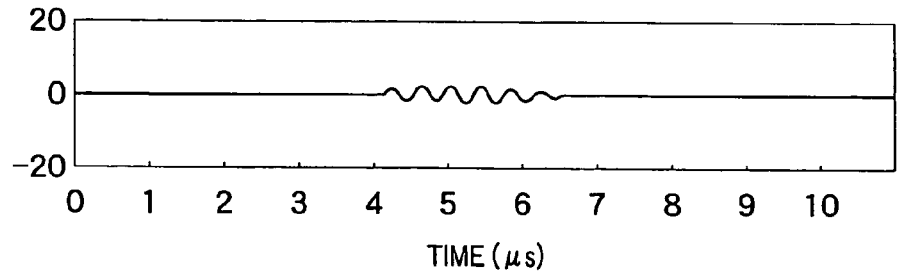

FIG. 8A shows the case where the reference ultrasonic beam of 16 ultrasonic beams is transmitted toward the direction (14°,0°), and FIGS. 8B to 8D show the waveforms of the drive signals applied to three ultrasonic transducers at the time of the transmission as examples. Further, FIG. 9A shows the case where the reference ultrasonic beam of 16 ultrasonic beams is transmitted toward the direction (7°,7°), and FIGS. 9B to 9D show the waveforms of the drive signals applied to three ultrasonic transducers at the time of the transmission as examples.

FIG. 10 is a histogram showing the maximum amplitudes of the drive signals applied to the respective ultrasonic transducers for transmitting 16 ultrasonic beams. In the histogram of FIG. 10, the lateral axis indicates the maximum amplitude and the longitudinal axis indicates the frequency of occurrence. Here, the maximum amplitude is represented by a relative value to the maximum amplitude for transmitting one ultrasonic beam. Further, four columns of each maximum amplitude value of the lateral axis correspond to the cases of FIGS. 6A to 9D, respectively. FIG. 11 is a table created based on the histogram.

As shown in FIGS. 10 and 11, in whichever direction 16 ultrasonic beams are transmitted, a state in which the maximum amplitude exceeds "12" never occurs. It is known that the maximum output voltages of the transmitting circuits may be set by being divided into plural kinds of ranks corresponding to the maximum amplitudes "1" to "12" applied to the respective ultrasonic transducers, based on the simulation result. By thus setting the plural kinds of maximum output voltages with respect to the plural transmitting circuits so as to correspond to the maximum amplitudes of the drive signals supplied to the respective ultrasonic transducers, the power consumption in the multibeam transmission can be reduced.

Furthermore, in whichever direction 16 ultrasonic beams are transmitted, the frequency at which the maximum amplitude becomes equal to or more than "8" is extremely low. From the result, it can be said that, when the maximum amplitude is equal to or more than "8", even if the maximum amplitude is replaced by "7", that hardly affects on the transmission beams. Alternatively, with respect to the respective ultrasonic transducers 11, information on one drive waveform may be generated by superposing plural drive waveforms while shifting the transmission timing with respect to some of the ultrasonic beams for which the transmission timing of the ultrasonic waves are superposed. By thus synthesizing the plural drive waveforms, the power consumption in the multibeam transmission can be further reduced.

FIG. 12 is a diagram for explanation of an example of the power consumption reduction in the multibeam transmission. In this example, the maximum output voltage of the transmitting circuit is given as "2" when the maximum amplitude of the drive signal is "1" or "2", the maximum output voltage of the transmitting circuit is given as "4" when the maximum amplitude of the drive signal is "3" or "4", the maximum output voltage of the transmitting circuit is given as "7" when the maximum amplitude of the drive signal is any one of "5" to "7", and the maximum output voltage of the transmitting circuit is given as "12" when the maximum amplitude of the drive signal is "12". Assuming that the power consumption of the transmitting circuit is proportional to the square of the maximum output voltage, and the proportionality factor is "1" for simplicity, the power consumption of the transmitting circuits is obtained as follows.

$$2^2 \times (128 + 627) + 4^2 \times (378 + 191) +$$
$$7^2 \times (16 + 33 + 19) + 12^2 \times 4 \approx 1.60 \times 10^4$$

On the other hand, when the maximum output voltages of all transmitting circuits are given as "12", the power consumption of the transmitting circuits is obtained as follows.

$$12^2 \times 1396 \approx 2.01 \times 10^5$$

Therefore, the reduction effect of the power consumption is as follows.

$$1.60 \times 10^4 / 2.01 \times 10^5 \approx 8\%$$

In the above described example, if the maximum output voltage of the transmitting circuits is given as "7" when the maximum amplitude of the drive signal exceeds "7", the power consumption can be further reduced.

Next, examples of the drive waveforms when the maximum amplitudes of the drive waveforms are replaced by a predetermined maximum amplitude will be described by referring to FIGS. 13A to 15D. Here, the case where the space of 60°×60° is scanned by 15×15 transmissions by simultaneously transmitting 4×4=16 transmission beams is assumed. Further, the longitudinal axes of FIGS. 15A to 15D indicate the relative amplitudes of the drive waveforms of the respective elements, and the amplitude when transmitted in one direction only is given as "1". Furthermore, the broken lines of FIGS. 15A to 15D are lines showing that the amplitude is equal to "4".

Figure 13A:
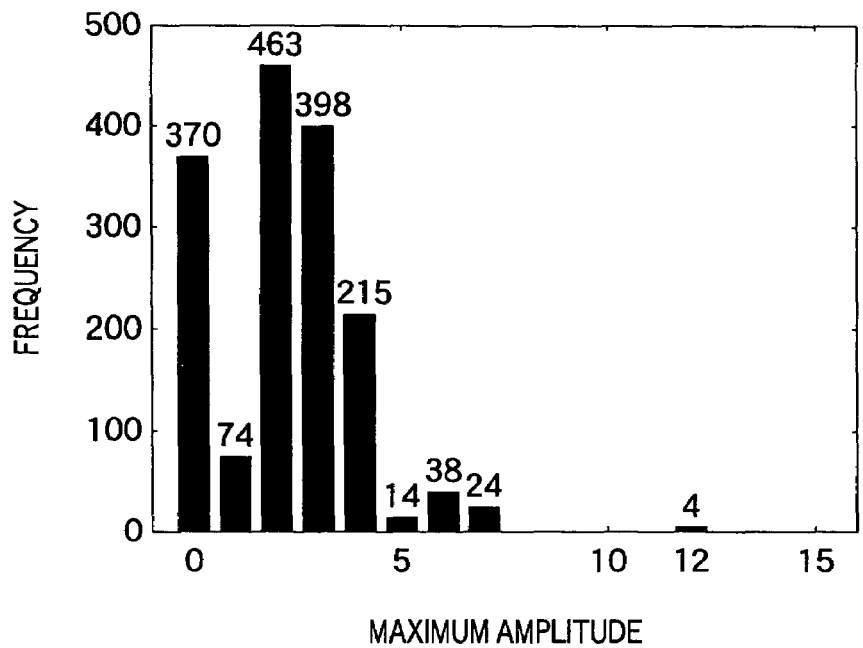
FIG. 13A shows an example of the result of obtaining the frequencies of the maximum amplitudes of the drive waveforms of the respective elements (ultrasonic transducers)
Figure 13B:
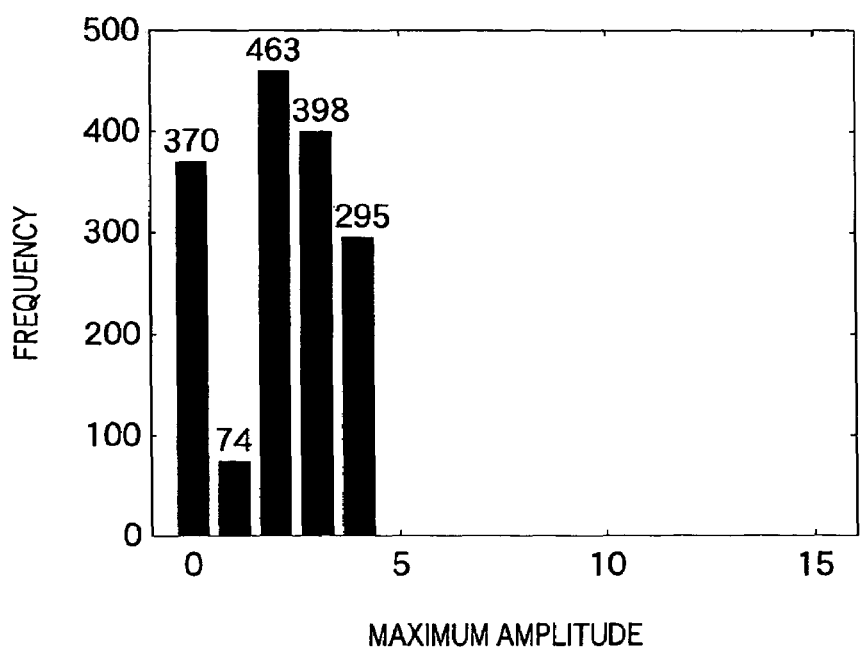
FIG. 13B shows the frequencies of the maximum amplitudes of the drive waveforms of the respective elements when the maximum amplitudes equal to or more than "5" shown in FIG. 13A are replaced by "4"

For example, assuming that the result of obtaining the frequencies of the maximum amplitudes of the drive waveforms of the respective elements (ultrasonic transducers 11) of the two-dimensional transducer array in the entire period of 15×15 transmissions is a result as shown in FIG. 13A. In this case, since the frequency at which the maximum amplitude becomes equal to or more than "5" is extremely lower than the frequency at which the maximum amplitude becomes equal to or less than "4", the maximum amplitudes of the drive waveforms of the respective elements having the maximum amplitudes equal to or more than "5" are replaced by "4" as shown in FIG. 13B.

Figure 14:
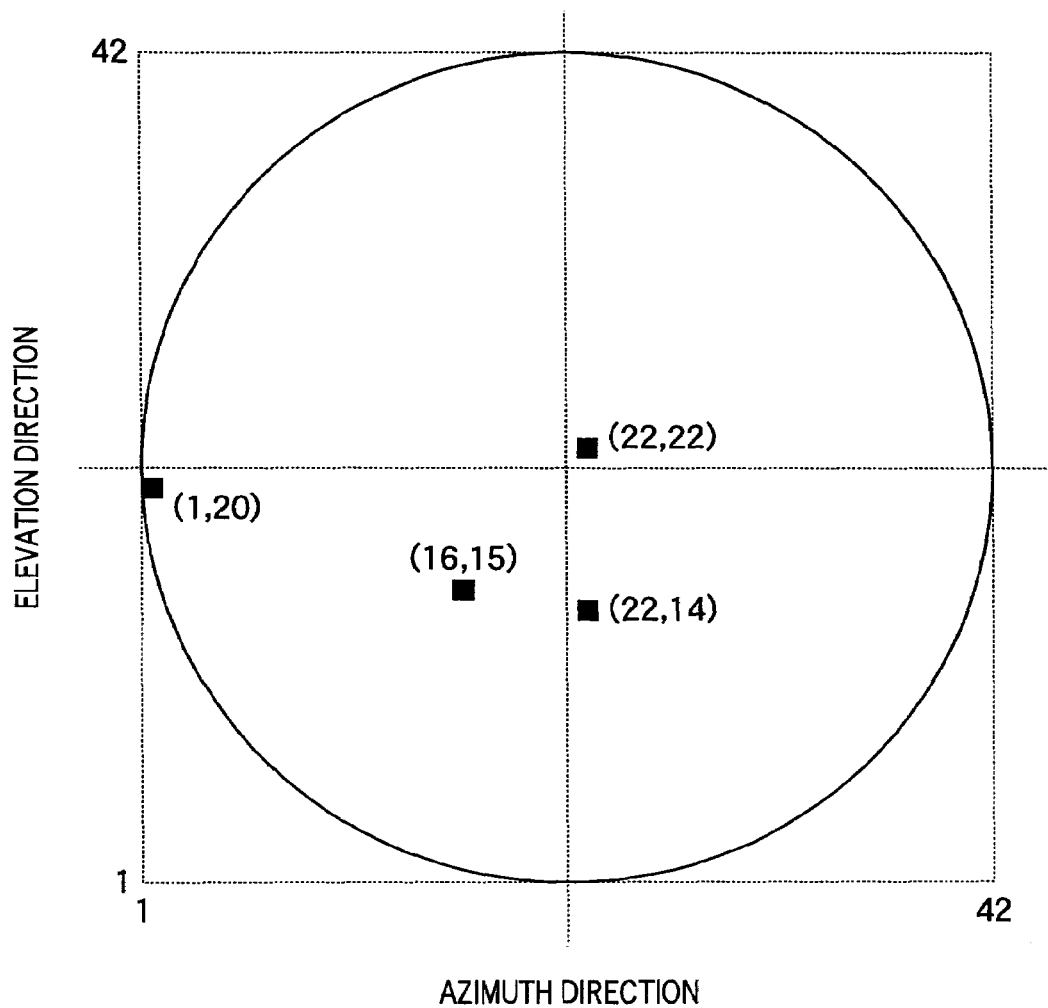
FIG. 14 is a diagram for explanation of expressing the positions of the respective elements of the two-dimensional transducer array of 42 elements×42 elements shown in FIG. 2 by coordinates (x,y)
Figure 15A:
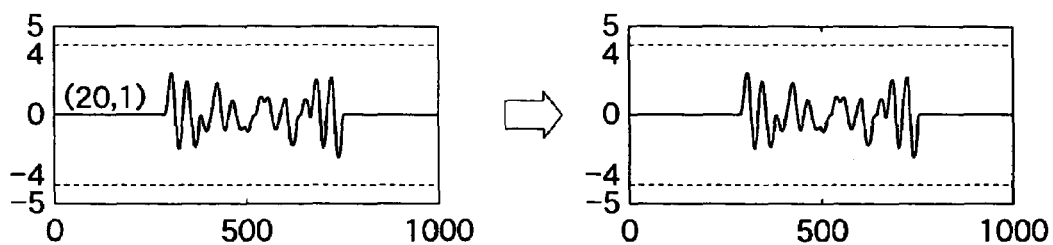
FIGS. 15A to 15D show examples of the drive waveforms when the maximum amplitudes of the drive waveforms of the respective elements are replaced by a predetermined maximum amplitude.
Figure 15B:
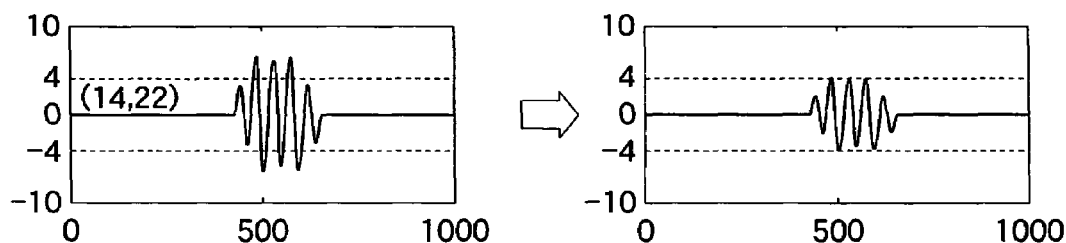
Figure 15C:
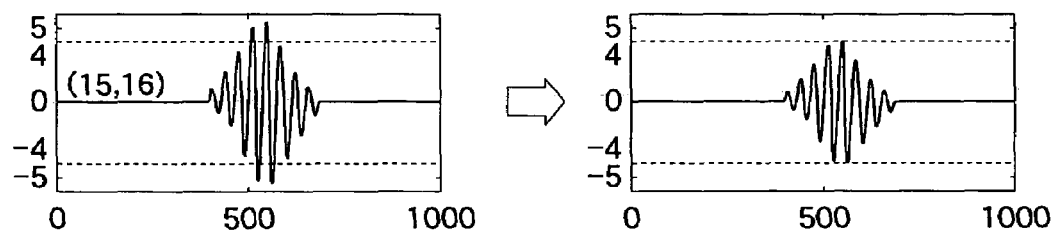
Figure 15D:
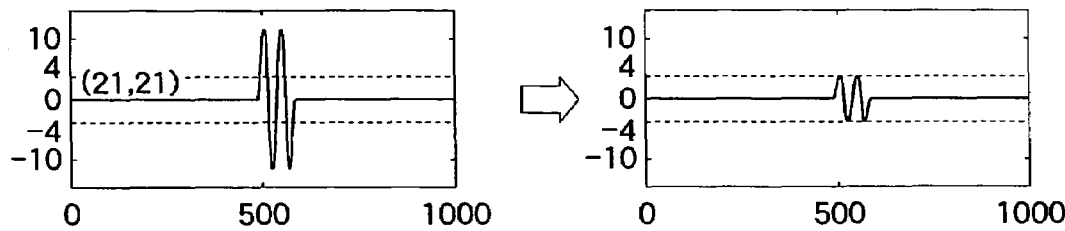
Figure 17A:
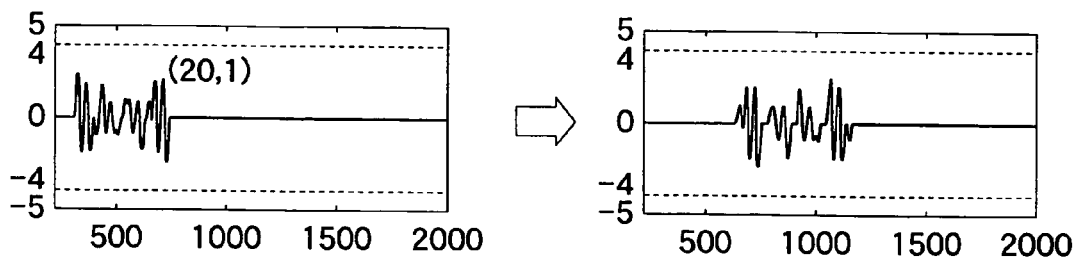
FIGS. 17A to 17D show examples of drive waveforms of the respective elements when the transmission timing is shifted.
Figure 17B:
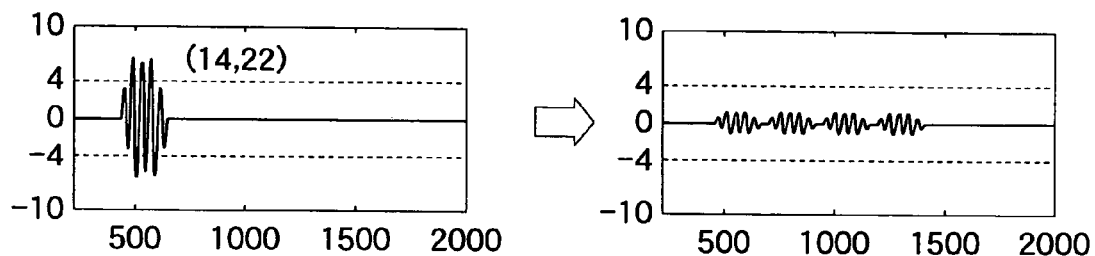
Figure 17C:
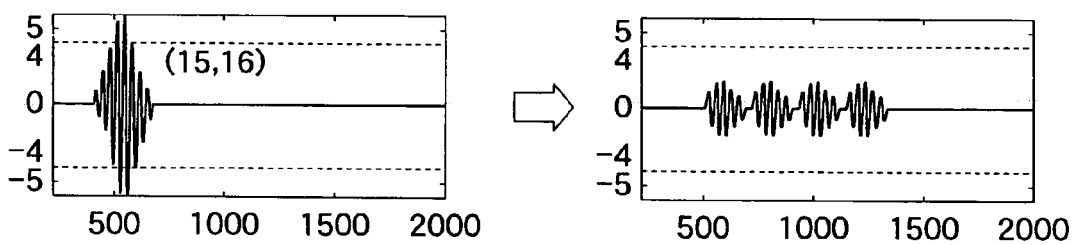
Figure 17D:
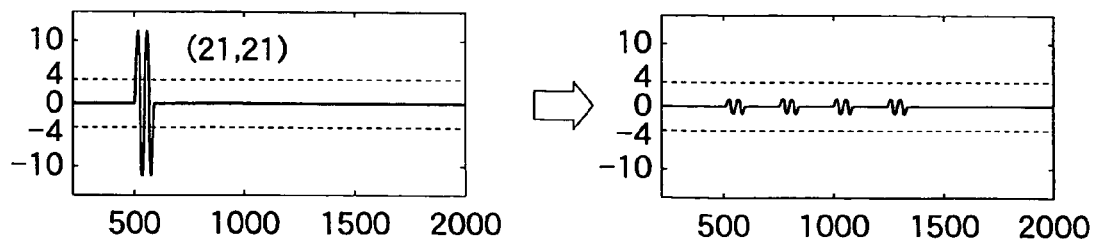

The positions of the respective elements of the two-dimensional transducer array of 42 elements×42 elements shown in FIG. 2 are expressed by coordinates (x,y) with the azimuth direction as the x axis and the elevation direction as the y axis as shown in FIG. 14. At this time, since the drive waveform of the element located at coordinates (20,1) has the maximum amplitude equal to or less than "4" as shown, in the left part of FIG. 15A, the replacement of the maximum amplitude is not performed with respect to the drive waveform of the element as shown in the right part of the same drawing. On the contrary, since the drive waveforms of three elements located at the coordinates (14,22), coordinates (15,16), and coordinates (21,21), respectively, have the maximum amplitudes exceeding "4" as shown in the left parts of FIGS. 15B to 15D, the drive waveforms of these elements are adjusted to the drive waveforms in which the maximum amplitudes are replaced by "4" as shown in the right parts of FIGS. 15B to 15D. Specifically, the drive waveform having the maximum amplitude exceeding "4" is adjusted to a drive waveform in which the maximum amplitudes is replaced by "4" by obtaining the maximum amplitude max of the drive wave form and multiplying the amplitude of the drive waveform by a coefficient (=4/max).

Next, examples of the drive waveforms when shifting the transmission timing with respect to some of the plural ultrasonic beams for which the transmission timing of the ultrasonic waves are superposed will be described by referring to FIGS. 16A to 17D. Here, as shown in FIG. 16A, each of the transmission beams is oriented toward the center of the scanning region of it, which is formed by being divided into small pieces. Further, as shown in FIGS. 16B to 16E, the case of dividing the transmission into four transmissions at intervals of 2.5 μs with four transmission beams in the elevation direction as one set is assumed. That is, after transmitting four transmission beams at the left end of FIG. 16B in the elevation direction as one set at time t=0, four transmission beams in the elevation direction are transmitted separately at four times while varying the azimuth direction at intervals of 2.5 μs as one set.

The positions of the respective elements (the ultrasonic transducers) of the two-dimensional transducer array of 42 elements×42 elements shown in FIG. 2 are expressed by coordinates (x,y) as shown in FIG. 14. Here, the maximum amplitudes of the drive waveforms of the respective elements are made smaller by shifting the transmission timing of the drive waveforms of four elements located at the coordinates (20,1), coordinates (14,22), coordinates (15,16), and coordinates (21,21), respectively from the transmission timing shown in the left parts of FIGS. 17A to 17D to the transmission timing shown in the right parts of FIGS. 17A to 17D, respectively. Note that the lateral axes of FIGS. 17A to 17D indicate the clock numbers, and the actual times are obtained by multiplying the numbers, which are indicated by the lateral axes, by 100 ns. Further, the longitudinal axes of FIGS. 17A to 17D indicate the relative amplitudes of the drive waveforms of the respective elements, and the amplitude when transmitted in one direction only is given as "1". Furthermore, the broken lines of FIG. 17A to 17D are lines showing that the amplitude is equal to "4".

Referring FIG. 1 again, the drive waveform synthesizing unit 32 generates information on a synthesized drive waveform by superposing the drive waveforms used for independently transmitting the ultrasonic beams from the ultrasonic probe 1 in the different directions, with respect to the respective ultrasonic transducers 11. Furthermore, the drive waveform synthesizing unit 32 may generate the information on the synthesized drive waveform by replacing the amplitude into the predetermined value in the case where the resultantly obtained amplitude of the drive waveform exceeds a predetermined value.

Further, in the transmitting circuits 21, the plural kinds of maximum output voltages are set so as to correspond to the maximum amplitudes of the drive signals supplied to the respective ultrasonic transducers. Thereby, the power consumption in these transmitting circuits 21 is reduced. By the way, the maximum output voltages of the respective transmitting circuit 21 are determined according to the power supply voltages supplied to the transmitting circuits 21. Accordingly, the plural kinds of power supply voltages are required, but these power supply voltages can be created by adding the plural power supplies.

For example, when the maximum supplied voltages to the respective transmitting circuits 21 are set to the minimum voltage required to output the maximum amplitude of the drive signal which corresponds to the synthesized drive waveform obtained by superposing the drive waveforms with respect to the sets of different transmitting directions, the plural kinds of minimum voltages exist with respect to the respective transmitting circuits 21, the power consumption is reduced in the transmitting circuits 21 in which the maximum supplied voltages are set to the smaller value.

The present invention can be utilized in an ultrasonic transmitting and receiving apparatus used for observing organs etc. within a living body by transmitting and receiving ultrasonic waves.

The invention claimed is:

1. An ultrasonic transmitting and receiving apparatus comprising:
   an ultrasonic probe including a plurality of ultrasonic transducers for forming ultrasonic beams according to a plurality of drive signals so as to transmit the ultrasonic beams to an object to be inspected, and receiving ultrasonic echoes reflected from the object so as to output a plurality of detection signals, respectively;
   drive waveform synthesizing means for generating information on a synthesized drive waveform obtained by synthesizing a plurality of drive waveforms with respect to each of said respective ultrasonic transducers in order to allow said ultrasonic probe to transmit a plurality of ultrasonic beams simultaneously in a plurality of different directions, by (i) superposing the plurality of drive waveforms, and replacing, when an amplitude of the drive waveform obtained as a result exceeds a predetermined value, the amplitude of the drive waveform by the predetermined value, and/or (ii) superposing the plurality of drive waveforms while shifting transmission timing with respect to some of a plurality of ultrasonic beams for which the transmission timing of ultrasonic waves are superposed;
   a plurality of transmitting circuits for generating a plurality of drive signals according to the information generated by said drive waveform synthesizing means so as to supply the plurality of drive signals to said plurality of ultrasonic transducers, respectively, plural kinds of maximum output voltages being determined so as to correspond to maximum amplitudes of the drive signals supplied to the respective ultrasonic transducers; and a plurality of receiving circuits for processing the plurality of detection signals outputted from said plurality of ultrasonic transducers which have received the ultrasonic echoes, respectively.

2. The ultrasonic transmitting and receiving apparatus according to claim 1, wherein said drive waveform synthesizing means generates, with respect to each of said ultrasonic transducers, the information on the synthesized drive waveform for simultaneously transmitting the ultrasonic beams in a plurality of different directions, by superposing a plurality of drive waveforms used in order to allow said ultrasonic probe to transmit the ultrasonic beams independently in the plurality of different directions.

3. The ultrasonic transmitting and receiving apparatus according to claim 2, wherein maximum supplied voltages to said respective transmitting circuits are set to minimum voltages necessary for outputting the maximum amplitude of the drive signal corresponding to the synthesized drive waveform obtained by superposing the plurality of drive waveforms with respect to plural sets of different transmission directions, and plural kinds of minimum voltages exist with respect to said respective transmitting circuits.

4. The ultrasonic transmitting and receiving apparatus according to claim 1, further comprising:

scanning control means for controlling said drive waveform synthesizing means to change the directions of the plurality of ultrasonic beams, which are transmitted from said ultrasonic probe, according to a predetermined beam scanning order.

* * * * *